United States Patent
Uslenghi et al.

(10) Patent No.: US 7,326,388 B2
(45) Date of Patent: *Feb. 5, 2008

(54) INDOOR AIR QUALITY MODULE WITH PIVOTAL INNER COMPARTMENT FOR SERVICABILITY OF MODULE COMPONENTS

(75) Inventors: Federico Uslenghi, Genoa (IT); Francesco Antonione, Milan (IT); Marco Occhetta, Milan (IT)

(73) Assignee: Carrier Corporation, Syracuse, NY (US)

(*) Notice: Subject to any disclaimer, the term of this patent is extended or adjusted under 35 U.S.C. 154(b) by 464 days.

This patent is subject to a terminal disclaimer.

(21) Appl. No.: 10/788,845

(22) Filed: Feb. 27, 2004

(65) Prior Publication Data

US 2005/0191219 A1    Sep. 1, 2005

(51) Int. Cl.
  *B01J 19/08* (2006.01)
(52) U.S. Cl. .................................... 422/186.3; 422/121
(58) Field of Classification Search ............ 422/186.3, 422/121
  See application file for complete search history.

(56) References Cited

U.S. PATENT DOCUMENTS

| | | | |
|---|---|---|---|
| 3,520,115 A * | 7/1970 | Bowen | ........................ 55/422 |
| 4,210,429 A | 7/1980 | Golstein | |
| 6,797,042 B2 * | 9/2004 | LaFerriere et al. | ........... 95/273 |
| 6,869,468 B2 | 3/2005 | Gibson | |
| 6,884,399 B2 * | 4/2005 | Reisfeld et al. | .......... 422/186.3 |
| 2005/0189210 A1 | 9/2005 | Uslenghi et al. | |

FOREIGN PATENT DOCUMENTS

JP    2000157621 A    6/2000

* cited by examiner

*Primary Examiner*—Kishor Mayekar
(74) *Attorney, Agent, or Firm*—Carlson, Gaskey & Olds

(57) ABSTRACT

An indoor air quality module includes an ultraviolet light source located between two titanium dioxide coated honeycombs. Photons of ultraviolet light are absorbed by the titanium dioxide coating to form reactive hydroxyl radicals that attack and oxidize contaminants in the to water, carbon dioxide, and other substances. An outer compartment is attached to an air duct and an HVAC unit, and a pivotally attached inner compartment supports the honeycombs and the ultraviolet light source. A first end of the inner compartment is pivotally attached to the outer component, and an opposing second end is removably attached to the outer compartment by fasteners. When servicing is required, the fasteners are removed to allow the inner compartment to pivot relative to the outer compartment to a vertical service position to allow access to the components in the inner compartment.

23 Claims, 4 Drawing Sheets

INDOOR AIR QUALITY MODULE WITH PIVOTAL INNER COMPARTMENT FOR SERVICABILITY OF MODULE COMPONENTS

BACKGROUND OF THE INVENTION

The present invention relates generally to an indoor air quality module including an inner compartment that contains the module components and pivotable between a working position and a servicing position that allows for servicing of the components.

Indoor air can include trace amounts of contaminants, including biospecies, dust, particles, odors, carbon monoxide, ozone, and volatile organic compounds (VOCs) such as formaldehyde, acetaldehyde, toluene, propanol, butene, etc. Indoor air quality modules are used to purify the air by destroying contaminants. The module includes a titanium dioxide coated monolith, such as a honeycomb, and an ultraviolet light source.

Titanium dioxide operates as a photocatalyst to destroy contaminants when illuminated with ultraviolet light. Photons of the ultraviolet light are absorbed by the titanium dioxide, promoting an electron from the valence band to the conduction band, thus producing a hole in the valence band and adding an electron in the conduction band. The promoted electron reacts with oxygen, and the hole remaining in the valence band reacts with water, forming reactive hydroxyl radicals. When contaminants in the air flow through the honeycomb and are adsorbed onto the titanium dioxide coating, the hydroxyl radicals attack and oxidize the contaminants to water, carbon dioxide, and other substances. The ultraviolet light also kills the biospecies in the airflow that are irradiated.

In prior indoor air quality modules, the ultraviolet light and the honeycombs are contained in an inner compartment. An outer compartment of the module is attached to the ceiling. Both ends of the inner compartment are attached to the outer compartment by fasteners, such as screws. When the components in the inner compartment need maintenance, the fasteners are removed. The inner compartment is generally pulled downwardly to separate the inner compartment from the outer compartment. The components in the inner compartment can then be disassembled on a working surface. A drawback to this prior indoor air quality modules is that two people are required to remove the inner compartment from the outer compartment because the fasteners must be removed from both ends of the module.

Hence, there is a need for an indoor air quality module that includes an inner compartment pivotable relative to the outer compartment to facilitate servicing of the components in the inner compartment.

SUMMARY OF THE INVENTION

An indoor air quality module (IAQ) purifies the air in an interior space. The module includes an ultraviolet light source located between two titanium dioxide coated honeycombs. When photons of ultraviolet light are absorbed by the titanium dioxide coating, reactive hydroxyl radicals are formed. When contaminants such as a volatile organic compounds or carbon monoxide flow through the honeycomb and adsorb onto the titanium dioxide coating, the hydroxyl radicals attack the contaminants. A hydrogen atom is abstracted from the contaminants, oxidizing the contaminants to water, carbon dioxide, and other substances. The module also decomposes ozone to oxygen and kills biospecies.

An inner compartment supports the honeycomb and the ultraviolet light source. An outer compartment is attached to an air duct and a satellite indoor unit. A first end of the inner compartment is pivotally attached to the outer component and pivotal between a working position and a servicing position, and an opposing second end of the inner compartment is removably attached to the outer compartment by fasteners.

During operation of the module, the inner compartment is substantially horizontal and received in the outer compartment. When servicing is required, the fasteners are removed, allowing the inner compartment to pivot relative to the outer compartment to a substantially vertical position. The honeycombs and the ultraviolet light source are exposed and can be removed, repaired, and maintained. When servicing is complete, the inner compartment is pivoted to the substantially horizontal position and secured by the fasteners.

These and other features of the present invention will be best understood from the following specification and drawings.

BRIEF DESCRIPTION OF THE DRAWINGS

The various features and advantages of the invention will become apparent to those skilled in the art from the following detailed description of the currently preferred embodiment. The drawings that accompany the detailed description can be briefly described as follows.

DETAILED DESCRIPTION OF THE PREFERRED EMBODIMENT

Figure 1:
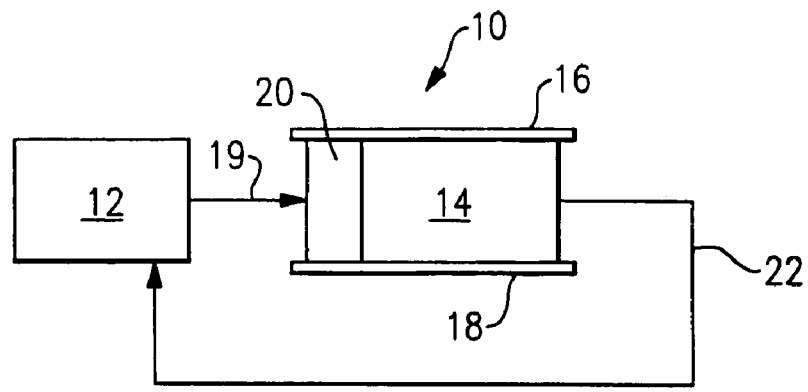
FIG. 1 schematically illustrates an enclosed environment, such as a building, vehicle or other structure, including an interior space and an HVAC system.

FIG. 1 schematically illustrates a structure 10, such as building or vehicle, that includes an interior space 12. The interior space 12 can be a room, an office or a vehicle cabin, such as a car, train, bus or aircraft. An HVAC system, such as a satellite indoor unit 14, heats or cools the interior space 12 of the structure 10. The satellite indoor unit 14 preferably is installed between a ceiling 16 and a false ceiling 18 in the structure 10. It should be understood that other arrangements will benefit from this invention.

Air in the interior space 12 is drawn into the satellite indoor unit 14 through an air duct 19. The satellite indoor unit 14 changes the temperature of the air drawn into the air duct 19. If the satellite indoor unit 14 is operating in a cooling mode, the air is cooled. Alternately, if the satellite indoor unit 14 is operating in a heating mode, the air is heated. The air is then returned to the interior space 12 through an air duct 22 to change the temperature of the air in the interior space 12.

An indoor air quality module 20 mounted between the air duct 19 and the satellite indoor unit 14 purifies the air before it is drawn into the satellite indoor unit 14. Alternately, the module 20 can purify the air leaving the satellite indoor unit 14 before returning into the interior space 12 or the module 20 can be a stand alone unit employed with the satellite indoor unit 14.

The indoor air quality module 20 oxidizes contaminants in the air, including volatile organic compounds, semi-volatile organic compounds and carbon monoxide, to water, carbon dioxide, and other substances. Examples of volatile organic compounds are aldehydes, ketones, alcohols, aromatics, alkenes, or alkanes. The indoor air quality module 20 also decomposes ozone to oxygen and kills biospecies.

Figure 2:
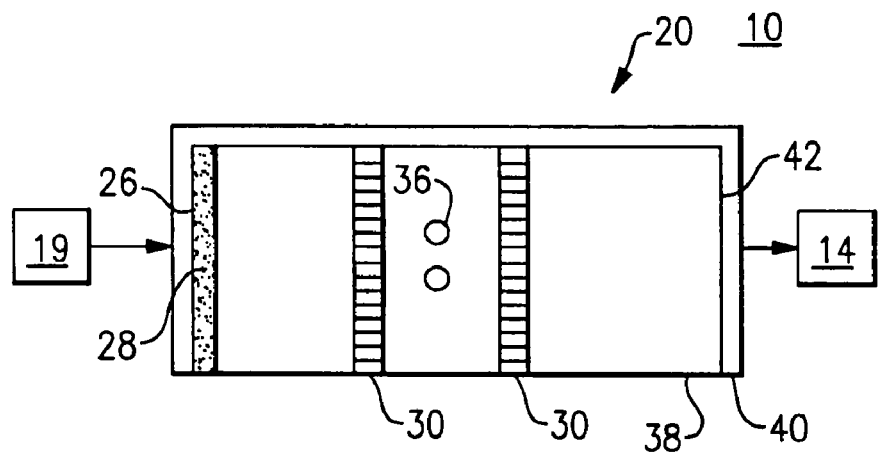
FIG. 2 schematically illustrates a side view of the indoor air quality module of the present invention.

FIG. 2 schematically illustrates a side view of the indoor air quality module 20 of the present invention. The indoor air quality module 20 defines a compartment. The air flows through a particle filter 28 that filters dust or other large particles from the air.

Figure 3:
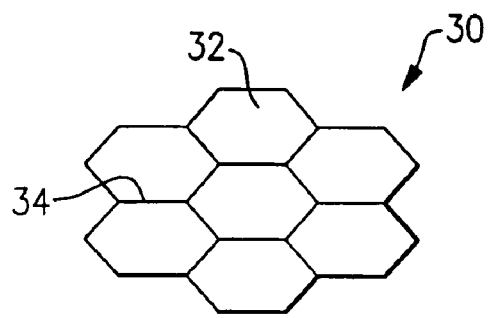
FIG. 3 schematically illustrates a front view of the honeycomb of the indoor air quality module.

The filtered air then flows through a monolith 30, such as a honeycomb 30 (FIG. 3). Preferably, there are at least two honeycombs 30 in the module 20 made of aluminum or an aluminum alloy. FIG. 3 schematically illustrates a front view of a portion of a honeycomb 30. The honeycomb 30 includes a plurality of hexagonal open passages 32 through which the air flows. The open passages 32 are coated with a photocatalytic coating 34, such as titanium dioxide. The titanium dioxide can also be doped or loaded with a metal oxide.

An ultraviolet light source 36 is positioned between the honeycombs 30. The ultraviolet light source 36 generates light having a wavelength in the range of 180 to 400 nanometers. If more than two honeycombs 30 are utilized in the module 20, the honeycombs 30 and the ultraviolet light source 36 alternate in the indoor air quality module 20. That is, an ultraviolet light source 36 is located between each of the honeycombs 30.

When illuminated by the ultraviolet light source 36, the titanium dioxide coating 34 on the honeycomb 30 is activated. Photons of ultraviolet light are absorbed by the titanium dioxide coating 34, promoting an electron from the valence band to the conduction band and producing a hole in the valence band. The electrons promoted to the conduction band are captured by oxygen. The holes in the valence band react with water molecules adsorbed on the titanium dioxide coating 34 to form reactive hydroxyl radicals.

When a volatile organic compound adsorbs onto the titanium dioxide coating 34, the hydroxyl radicals attack the volatile organic compound, abstracting a hydrogen atom from the volatile organic compound. The hydroxyl radicals oxidize the volatile organic compounds and produce water, carbon dioxide, and other substances. The purified air then exits the indoor air quality module 20 through an outlet 42.

As air flow through the module 20, the particle filter 28 acts as a mechanical filter to remove dust and particles. When illuminated by the ultraviolet light source 36, the titanium dioxide coated 34 honeycombs 30 oxidize and destroy volatile organic compounds. Finally, the ultraviolet light generated by the ultraviolet light source 36 has a germicidal effect to kill biospecies.

The indoor air quality module 20 further includes an outer component 40 and an inner compartment 38 that contains the particle filter 28, the honeycombs 30 and the ultraviolet light source 36 and is pivotally attached to the outer component 40. The outer compartment 40 is attached to the air duct 19 and to the satellite indoor unit 14 and houses the electric, electronic and safety related components. During operation of the module 20, the inner compartment 38 is contained in the outer compartment 40.

Figure 4:
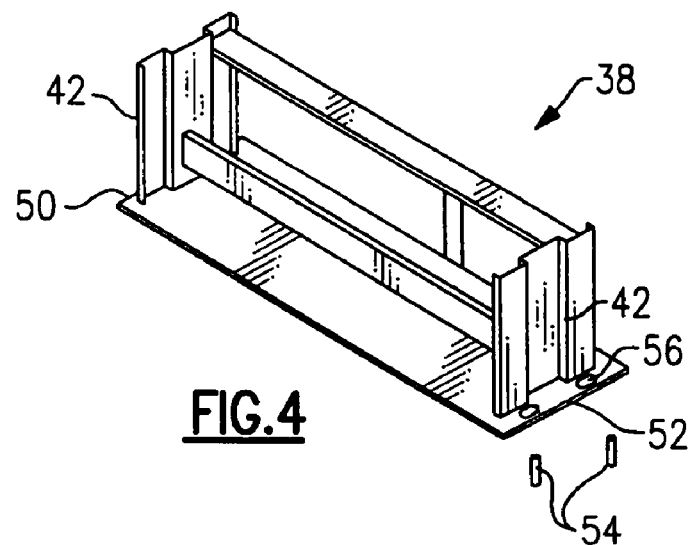
FIG. 4 schematically illustrates the inner compartment without any internal components.

FIG. 4 schematically illustrates the inner compartment 38 of the indoor air quality module 20 without the filter 28, the honeycombs 30, and the ultraviolet light source 32. The inner compartment 38 includes a first end 50 pivotally attached to the outer component 40, an opposing second end 52, and opposing side portions 42 that support the filter 28, the honeycomb 30 and the ultraviolet light source 32. The side portions 42 prevent these components from accidentally disengaging from the inner compartment 38. When installed in the inner compartment 38, the honeycombs 28 and the ultraviolet lights 24 are parallel. The pivotal attachment of the inner compartment 38 to the outer compartment 40 allows maintenance of the module 20 to be done by a single person.

The second end 52 of the inner compartment 38 is removably attached to the outer compartment 40 by fasteners 54, such as screws. In one example, two fasteners 54 are employed to secure the second end 52 to the outer compartment 40. By utilizing two fasteners 54, additional security is provided to maintain the inner compartment 38 within the outer compartment 40. Each fastener 54 is received in an aperture 56 in the inner compartment 38 that aligns with an aperture (not shown) in the outer compartment 40 to secure the inner compartment 38 inside the outer compartment 40.

Figure 5:
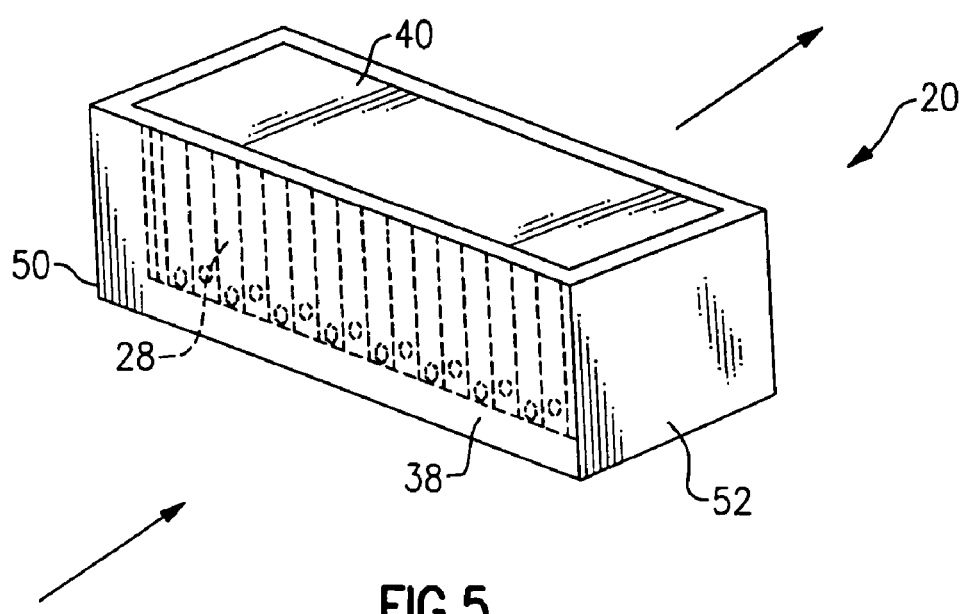
FIG. 5 schematically illustrates the indoor air quality module in the horizontal working position.

FIG. 5 schematically illustrates the indoor air quality module 20 during operation when the inner component 38 is received in the outer compartment 40 and in the horizontal working position to clean the air flowing through the module 20.

Figure 6:
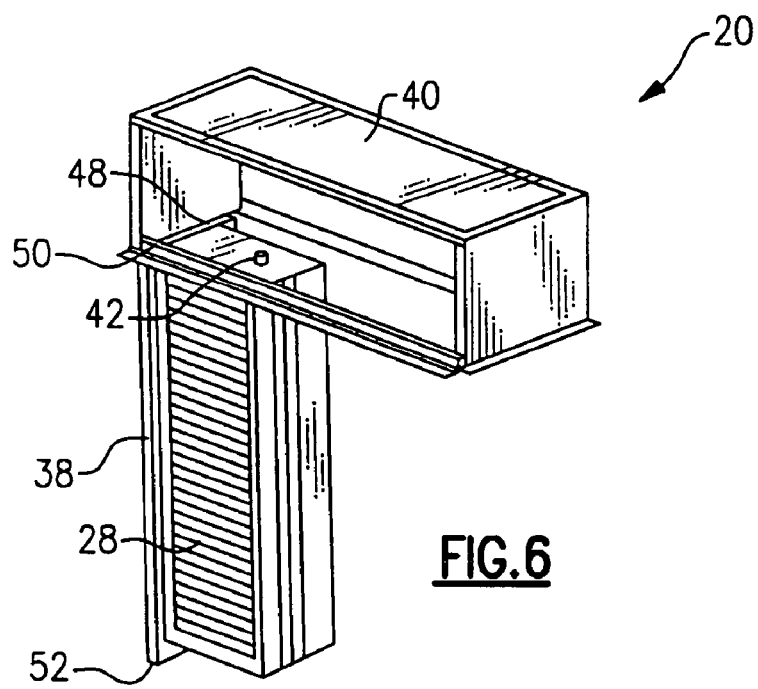
FIG. 6 schematically illustrates the indoor air quality module in the vertical service position.

When servicing is required, the fasteners 54 are removed from the second end 52 of the inner compartment 38. The inner compartment 38 is then pivoted relative to the outer component 40 about the first end 50 to the vertical service position shown in FIG. 6. In this position, an operator can access to the air filter 28, the honeycombs 30, and the ultraviolet light source 36 in the inner compartment 38. In the vertical position, the inner compartment 38 is substantially perpendicular to the outer compartment 40. Maintenance and service operations can be accomplished without removing the indoor air quality module 20, the air duct 19, or the indoor satellite unit 14. When in the vertical position, the side support portions 42 support the internal components and prevents them from falling out of the inner compartment 38.

When servicing is complete, the inner compartment 38 is pivoted relative to the outer compartment 40 about the first end 50 and into the horizontal position of FIG. 5. The attachment members 54 reinserted into the aligned apertures 56 of the inner compartment 40 and the apertures of the outer compartment 40 employed to secure the inner compartment 40 in the horizontal position.

Figure 7:
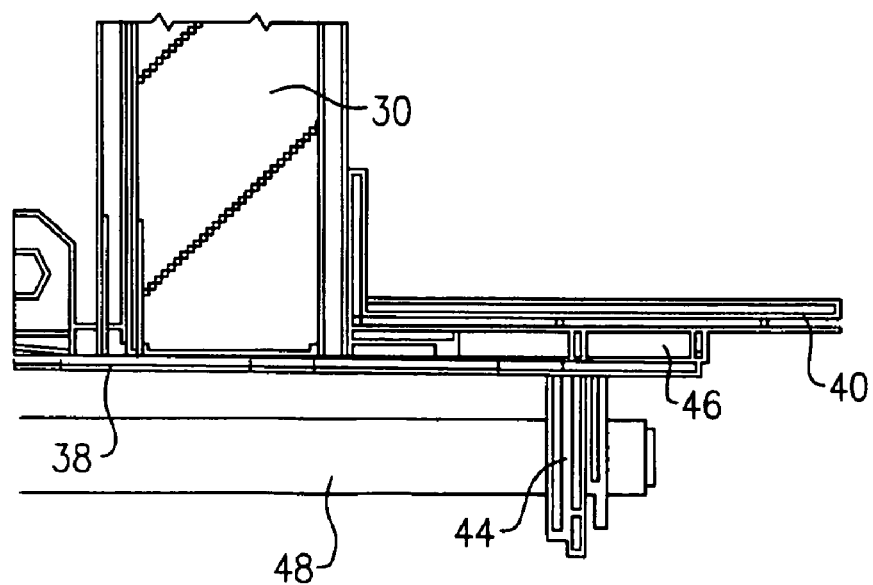
FIG. 7 schematically illustrates a first embodiment of a hinge that pivotally attaches the inner compartment to the outer compartment.

FIG. 7 schematically illustrates a first embodiment of the pivotal attachment of the first end 50 of the inner compartment 38 to the outer compartment 40. An inner hinge 44 is attached to each of the opposing sides of the first end 50 of the inner compartment 38, and an outer hinge 46 is attached to each of the opposing sides of the first end 50 of the outer compartment 40. That is, two inner hinges 44 and two outer hinges 46 are employed, although FIG. 7 only illustrates one inner hinge 44 and one outer hinge 46. The inner hinges 44 and the outer hinges 46 receive a pivot bar 48 that allows the inner compartment 38 to pivot with respect to the outer compartment 40. When the inner compartment 38 is pivoted relative to the outer compartment 40, the inner hinges 44 pivot about the pivot bar 48 to allow the inner compartment 38 to pivot. That is, the outer compartment 40 is stationary, and the inner compartment 38 pivots about the pivot bar 48 relative to the outer compartment 40.

Figure 8:
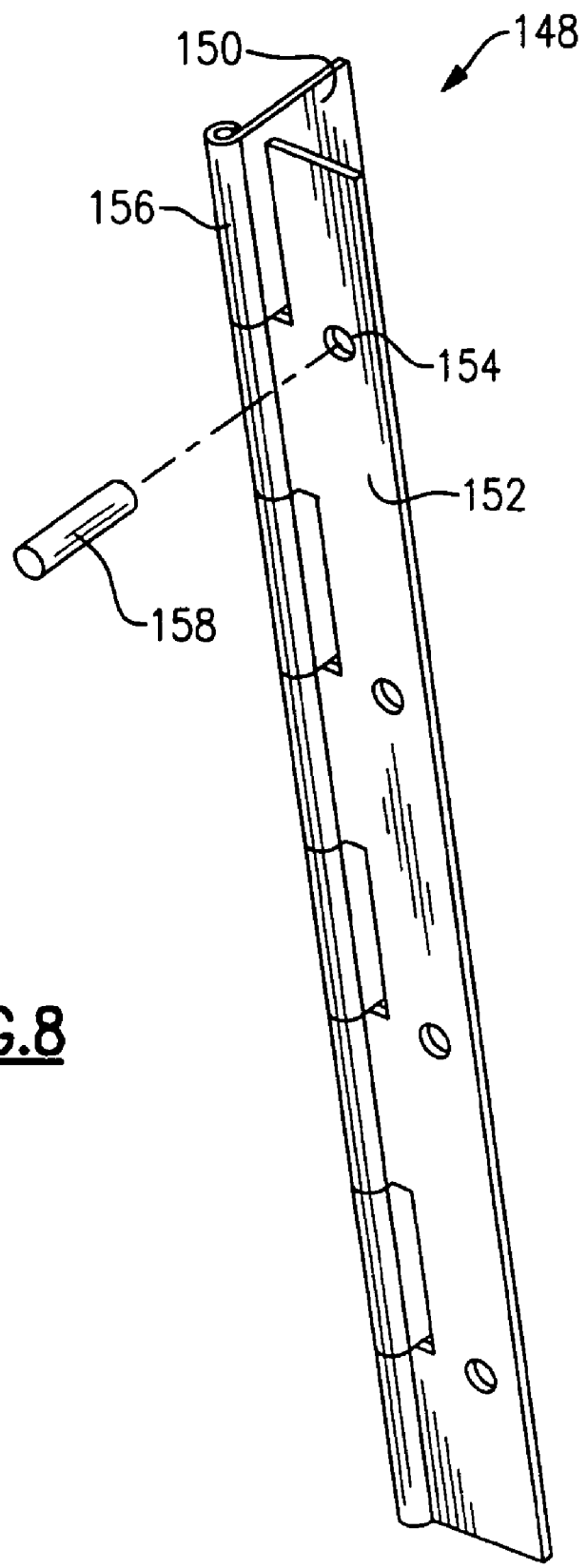
FIG. 8 schematically illustrates a second embodiment of a hinge that pivotally attaches the inner compartment to the outer compartment.

FIG. 8 schematically illustrates a second embodiment of a pivot 148 that pivotally attaches the first end 50 of the inner compartment 38 to the outer compartment 40. The pivot 148 includes an inner hinge 152 attached to the inner compartment 38 and an outer hinge 154 attached to the outer compartment 40. The hinges 152 and 154 are attached to the inner component and the outer component 40, respectively, by fasteners 158 that pass through apertures 154 in the hinges 152 and 154. The outer hinge 154 is pivotal relative to the inner hinge 152 by a pivot bar 156. When the inner compartment 38 is pivoted relative to the outer compartment 40, the inner hinge 152 pivots about the pivot bar 156 relative to the outer hinge 150 to allow the inner compartment 38 to pivot relative to the outer compartment 40.

Although two types of pivotal attachment have been illustrated and described, it is to be understood that any type of pivotal attachment can be employed to pivotally attached the inner compartment 38 to the outer compartment 40.

The foregoing description is only exemplary of the principles of the invention. Many modifications and variations of the present invention are possible in light of the above teachings. The preferred embodiments of this invention have been disclosed, however, so that one of ordinary skill in the art would recognize that certain modifications would come within the scope of this invention. It is, therefore, to be understood that within the scope of the appended claims, the invention may be practiced otherwise than as specifically described. For that reason the following claims should be studied to determine the true scope and content of this invention.

What is claimed is:

1. An indoor air quality module comprising:
an outer compartment attachable to a component; and
an inner compartment pivotally attached to the outer compartment and pivotal between a first position and a second position, the inner compartment having an inlet, an outlet, a monolith located between the inlet and the outlet, a photocatalytic coating applied on the monolith, and an ultraviolet light source to activate the photocatalytic coating.

2. The module as recited in claim 1 wherein the component is an air duct.

3. The module as recited in claim 1 wherein the inner compartment includes a first end and an opposing second end, and the first end of the inner compartment is pivotally attached to the outer compartment.

4. The module as recited in claim 3 wherein the opposing second end of the inner compartment is removably attached to the outer compartment by a fastener.

5. The module as recited in claim 4 wherein the fastener is a screw.

6. The module as recited in claim 1 wherein the inner compartment is substantially parallel to the outer compartment in the first position and the inner compartment is substantially perpendicular to the outer compartment in the second position.

7. The module as recited in claim 6 wherein said inner compartment is substantially horizontal in the first position and the inner compartment is substantially vertical in the second position.

8. The module as recited in claim 1 wherein the photocatalytic coating is titanium dioxide.

9. The module as recited in claim 1 wherein the monolith comprises a honeycomb.

10. The module as recited in claim 9 wherein the honeycomb comprises a plurality of hexagonal shaped passages coated with the photocatalytic coating.

11. The module as recited in claim 1 wherein the monolith defines a first monolith and a second monolith, and the ultraviolet light source is located between the first monolith and the second monolith.

12. The module as recited in claim 1 wherein the first position is substantially horizontal and the second position is substantially vertical.

13. The module as recited in claim 1 wherein the inner compartment houses a particle filter.

14. The module as recited in claim 1 wherein the inner compartment includes opposite side portions that support the monolith.

15. The module as recited in claim 1 wherein the inner compartment includes a first hinge and the outer compartment includes a second hinge, and the first hinge is pivotable about a pivot bar to pivot the inner compartment between the first position and the second position relative to the outer compartment.

16. The module as recited in claim 1 wherein the inner compartment and the outer compartment each include at least two hinges, the hinges receive a pivot bar, and the at least two hinges of the inner compartment pivot about the pivot bar to move the inner compartment between the first position and the second position.

17. An indoor air quality module comprising:
an outer compartment attachable to a component;
an inner compartment pivotally attached to the outer compartment and pivotal between a first position and a second position, the inner compartment having an inlet, an outlet, a first end pivotally attached to the outer compartment, an opposing second end, a monolith located between the inlet and the outlet, a titanium dioxide coating applied on the monolith, and an ultraviolet light source to activate the photocatalytic coating; and
a fastener to secure the opposing second end of the inner compartment to the outer compartment when the inner compartment is in the first position, removal of the fastener allowing the inner compartment to pivot relative to the outer compartment.

18. A method of purifying air comprising the steps of:
pivotally attaching an inner compartment to an outer compartment;
flowing air through a monolith having a photocatalytic coating;
illuminating the photocatalytic coating with an ultraviolet light source to activate the photocatalytic coating; and
pivoting the inner compartment between a first position and a second position.

19. The method as recited in claim 18 wherein the first position is substantially perpendicular to the second position.

20. The method as recited in claim 18 wherein the first position is substantially horizontal and the second position is substantially vertical.

21. The method as recited in claim 18 further comprising the step of attaching the outer compartment to a component.

22. The method as recited in claim 18 wherein the first position prevents access to the monolith and the ultraviolet light source and the second position allows access to the monolith and the ultraviolet light source.

23. The method as recited in claim 18 wherein the inner compartment houses a particle filter, and the step of flowing air includes flowing air through the particle filter to filter the air.

\* \* \* \* \*